United States Patent [19]

Trenner

[11] Patent Number: 4,979,943
[45] Date of Patent: Dec. 25, 1990

[54] SINGLE USE HYPODERMIC SYRINGE

[76] Inventor: Lewis E. Trenner, 3046 Gaylord St., Denver, Colo. 80210

[21] Appl. No.: 493,971

[22] Filed: Mar. 15, 1990

[51] Int. Cl.⁵ .............................................. A61M 5/00
[52] U.S. Cl. ..................................... 604/110; 604/208
[58] Field of Search ....................... 604/110, 208, 210

[56] References Cited

U.S. PATENT DOCUMENTS

| 4,391,272 | 7/1983 | Staempfli | 604/110 |
| 4,493,703 | 1/1985 | Butterfield | 604/110 |
| 4,731,068 | 3/1988 | Hesse | 604/110 |
| 4,781,684 | 11/1988 | Trenner | 604/110 |

FOREIGN PATENT DOCUMENTS

| 8902287 | 3/1989 | Switzerland | 604/110 |
| 8904187 | 5/1989 | Switzerland | 604/110 |

Primary Examiner—Stephen C. Pellegrino
Assistant Examiner—Michael Rafa

[57] ABSTRACT

A single use hypodermic syringe is provided and has a reversible stop member which permits movement of the plug in one direction but not in the opposite direction so that the plug may be moved in the direction to aspirate fluid in the hypodermic syringe during which the reversing member moves into a reversing chamber so that it may be reversed to permit movement of the plug to eject fluid from the hypodermic syringe but to prevent movement of the plug in the opposite direction after the ejection of fluid has been commenced and after all of the fluid has been ejected.

20 Claims, 2 Drawing Sheets

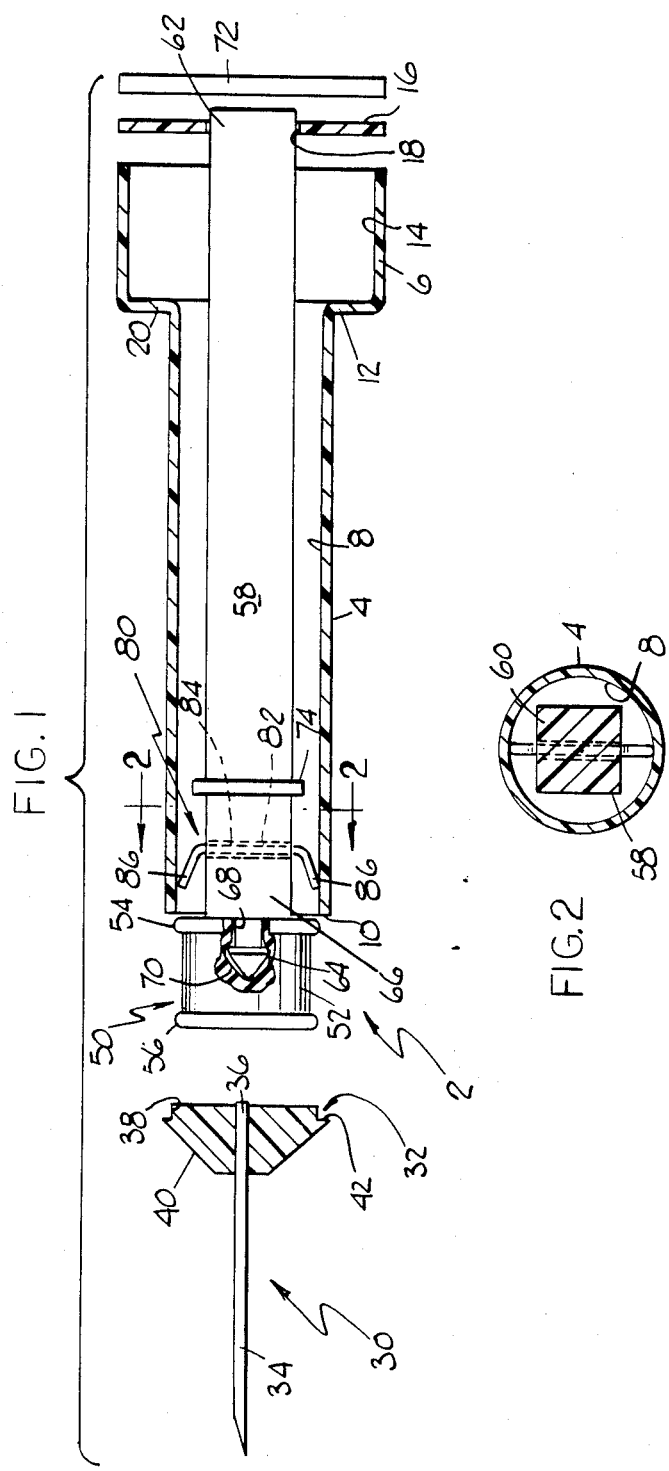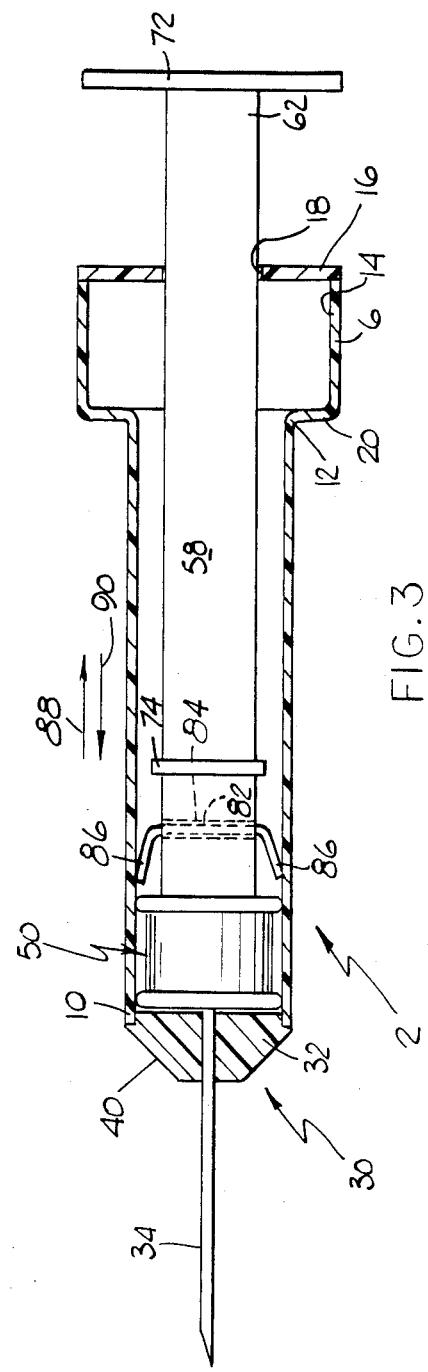

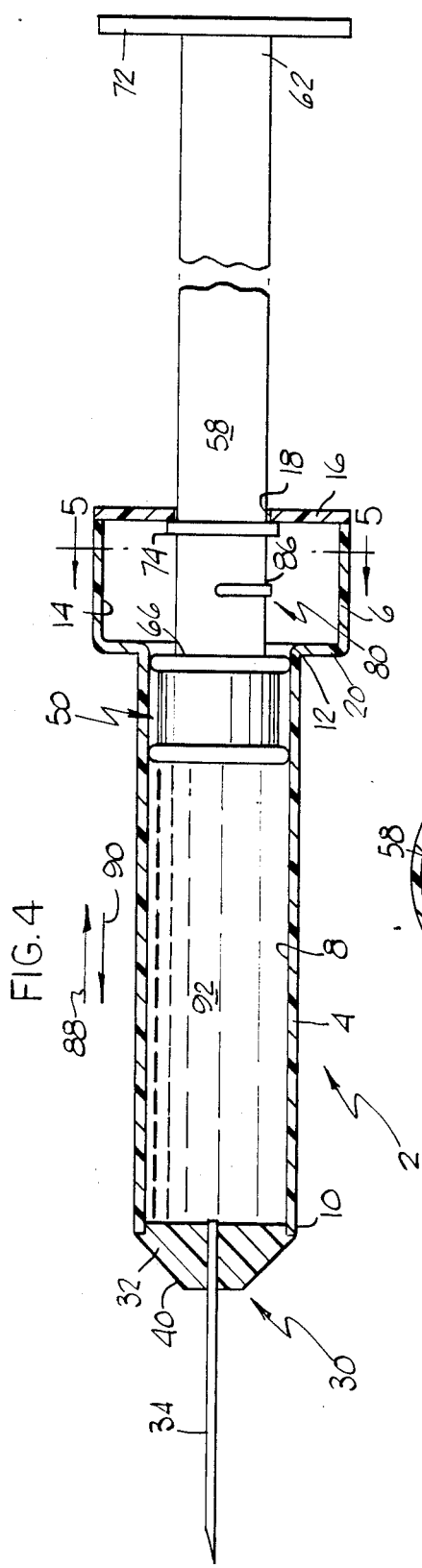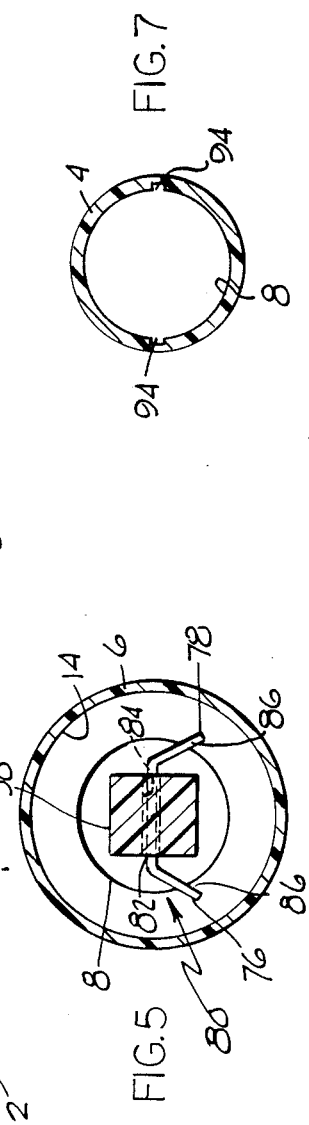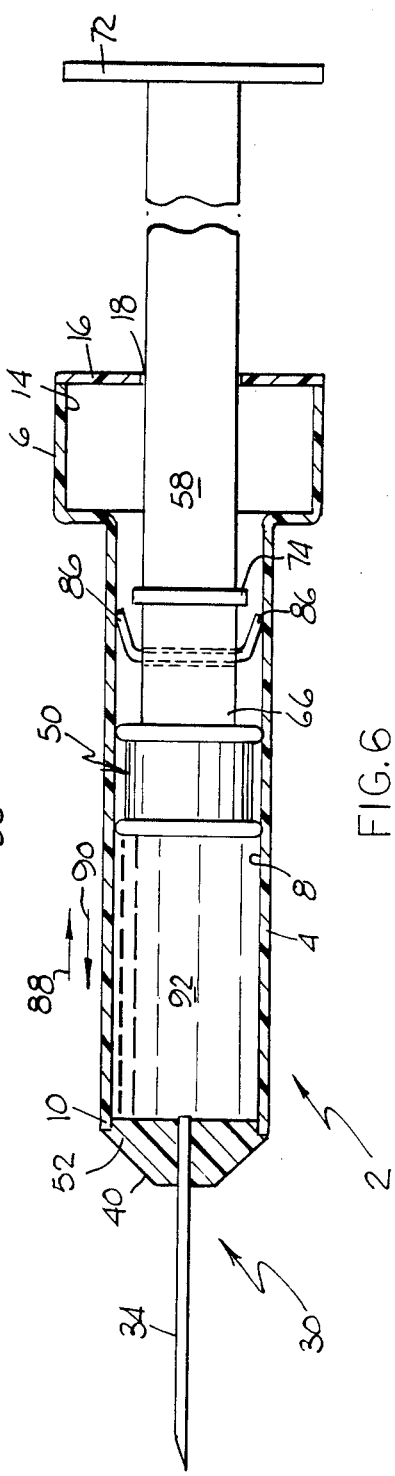

SINGLE USE HYPODERMIC SYRINGE

FIELD OF THE INVENTION

This invention relates generally to the field of hypodermic syringes which are used to inject a desired fluid into the body for various purposes and more specifically to the field of a single use disposable hypodermic syringe which is particularly suited to prevent transmission of diseases from one body to another body.

BACKGROUND OF THE INVENTION

These are many instances wherein it is highly desirable that a hypodermic syringe be capable of only a single use. This occurs many times in hospitals or other areas of medical treatment. The present concern relative to the spread of Acquired Immune Deficiency Syndrome, commonly called AIDS, reaffirms the need for a single use hypodermic syringe. A problem that exists particularly in relation to drug addicts is that the means associated with the hypodermic syringe for permitting only a single use must be of a nature that the function thereof cannot be readily removed by the drug addict. Applicant has provided such a single use hypodermic syringe.

BRIEF DESCRIPTION OF THE INVENTION

This invention provides a single use hypodermic syringe having a reversible stop means for permitting movement of the plug means of the hypodermic syringe in one direction but preventing movement of the plug means in the opposite direction during the aspiration of fluid into the hypodermic syringe, and during or after the ejection of the fluid from the hypodermic syringe to prevent the reloading of the hypodermic syringe.

In a preferred embodiment of the invention, the hypodermic syringe comprises a barrel portion having a generally cylindrical inner surface and an integral reversing chamber having a cross-sectional configuration larger than the barrel portion formed from a plastic material. The reversing chamber has an end wall which is secured thereto by suitable means, such as by welding. Needle means are provided for permitting fluid to be drawn into or ejected from the barrel portion. The needle means comprise a plastic body having a hollow needle projecting outwardly therefrom. The plastic body portion has a generally cylindrical outer surface having a diameter slightly less than the diameter of the generally cylindrical inner surface of the barrel portion so that the plastic body portion may be inserted into the barrel portion and secured thereto by suitable means, such as by welding, to form a fluid tight seal between the inner and outer surfaces. Plug means are located within the barrel portion and are in sealing engagement with the generally cylindrical inner surface. Rod means are provided and comprise an elongated rod having the plug means releasably secured to one end thereof and a handle portion secured to the other end thereof. The elongated rod extends outwardly through an opening in the end wall of the reversing chamber so that the handle may be grasped to reciprocate the plug means to draw fluid into or eject fluid out of the main body portion. An abutment shoulder is formed on the elongated rod to contact the portions of the end wall of the reversing chamber surrounding the opening therein so as to limit the movement of the elongated rod in one direction. The cross-sectional configuration of the elongated rod and the opening cooperate to prevent rotation of the elongated rod. Reversible stop means are mounted on the elongated rod between the plug means and the abutment shoulder and function to permit movement of the plug means in one direction but to prevent movement of the plug means in the opposite direction during the aspiration of fluid into the barrel portion and during or after the ejection of fluid from the barrel portion. The reversible stop means comprise a pin member having a central body portion located in an opening extending through the elongated rod for rotation about an axis transverse to the direction of movement of the elongated rod. Two integral leg portions extend outwardly from the opening in the elongated rod and when in the barrel portion, they extend in radial and axial directions and are in resilient contact with the generally cylindrical inner surface of the barrel portion.

The single use hypodermic syringe is marketed with the plug means in contact with or substantially in contact with the plastic body of the needle means with the ends of the leg portions facing the needle means. In operation, the hollow needle is placed into the desired fluid and the handle is pulled to aspirate the fluid into the barrel portion. The handle is pulled until the abutment shoulder prevents further movement thereof. At this position, the pin member is in the reversing chamber where it is free to rotate. When it is desired to eject the fluid from the barrel portion, the handle is pushed to move the plug means toward the needle means. As the elongated rod is moved, the leg portions contact the end of the generally cylindrical inner surface of the barrel portion and the central body portion of the pin member rotates so that the ends of the leg portions face the handle. During or after the ejection of the fluid from the barrel portion, the ends of the leg portions will prevent movement of the plug means in the aspiration direction by digging into the generally cylindrical inner surface.

BRIEF DESCRIPTION OF THE DRAWINGS

An illustrative and presently preferred embodiment of the invention is shown in the accompanying drawings in which:

FIG. 1 is a partially exploded elevational view with parts in section of a single use hypodermic syringe of this invention;

FIG. 2 is a cross-sectional view taken on the line 2—2 of FIG. 1;

FIG. 3 is an elevational view with parts in section illustrating a single use hypodermic syringe of this invention ready for use;

FIG. 4 is an elevational view with parts in section illustrating a single use hypodermic syringe of this invention after the fluid has been aspirated therein;

FIG. 5 is a cross-sectional view taken on the line 5—5 of FIG. 4;

FIG. 6 is an elevational view with parts in section illustrating a single use disposable hypodermic syringe of this invention during the ejection of the fluid; and FIG. 7 is a cross-sectional view illustrating a different barrel portion.

DETAILED DESCRIPTION OF THE INVENTION

A single use disposable hypodermic syringe 2 is illustrated in the drawings and has a barrel portion 4 and a reversing chamber 6 integral therewith which are integrally molded using a plastic material, such as polypropylene or other plastic materials having similar characteristics. The barrel portion 4 has a generally cylindrical inner surface 8 and first and second end portions 10 and 12. The reversing chamber 6 has a generally cylindrical inner surface 14 having a diameter greater than the diameter of the inner surface 8 for purposes described below. An end wall 16 having an opening 18 formed therein is secured to the reversing chamber by suitable means, such as by welding. A radially inwardly extending wall 20 extends between the inner surface 14 and the second end portion 12.

Needle means 30 are provided and comprise a plastic body portion 32 and a hollow needle 34 having a portion 36 thereof embedded in the plastic body portion 32. The plastic body portion 32 has a generally cylindrical outer surface portion 38 and a generally conical outer surface portion 40 which has a diameter greater than the diameter of the outer surface portion 38 to form an abutment shoulder 42. The diameter of the outer surface portion 38 is substantially the same as the diameter of the inner surface 8. The needle means 30 are secured to the first end portion 10 by inserting the outer surface portion 38 into the first end portion 10 until the abutment shoulder contacts the first end portion 10. Welding apparatus (not shown) is then used to weld the plastic body portion 32 to the first end portion in a fluid tight relationship. The plastic body portion 32, the barrel portion 4 and the reversing chamber 6 are preferably formed using the same type of plastic material such as a polypropylene or other plastic material having similar characteristics.

Plug means 50 are provided and comprise a body portion 52 having a pair 54 and 56 of radially outwardly projecting continuous cylindrical outer surfaces. Each of the outer surfaces 54 and 56 has a diameter slightly greater than the diameter of the inner surface 8 so as to be in a sealing relationship therewith. The plug means 50 are molded using a resilient material such as polybutadylene or polyisobutylene rubber. An elongated rod 58 having a non-circular cross-sectional configuration 60, such as a square, is provided and has a first end portion 62 which passes through the opening 18. The cross-sectional configuration of the opening 18 is the same as the cross-sectional configuration 60 of the elongated rod 58 to prevent rotation of the elongated rod 58. A spear head 64 is integral with a second end portion 66 of the elongated rod 58. The body portion 52 has a cylindrical passageway 68 leading to a cavity 70 which is dimensioned similarly to the spear head 64 so that it may be positioned therein. As illustrated in FIG. 1, the spear head 64 is larger than the passageway 68 so that the plug means 50 will move in either axial direction in the barrel portion 4 with the elongated rod 58. The passageway 68 and the cavity 70 cooperate with the spear head 64 to secure the plug means 50 to the elongated rod 58. A handle 72 is secured to the first end portion 62 by suitable means, such as by welding. An abutment shoulder 74 is formed on the elongated rod 58 and cooperates with the portions of the end wall 16 surrounding the opening 18 to limit the axial movement of the elongated rod 58. The elongated rod 58 is molded using a plastic material such as polypropylene or other materials having similar characteristics.

Reversible stop means 80 are provided and comprise a central body portion 82 having a cylindrical outer surface which is rotatably mounted in an opening 84 having a cylindrical inner surface extending through the elongated rod 58. The axial extent of the central body portion 82 is greater than the axial extent of the opening 84 and the diameter of the cylindrical inner surface of the opening 84 is sufficiently larger than the diameter of the cylindrical outer surface of the central body portion 82 so that the central body portion 82 is freely rotatable in the opening 84. The opening 84 is located between the spear head 64 and the abutment shoulder 74. The central body portion 82 has integral leg portions 86 which, when the central body portion 82 is radially opposite to the inner surface 8, extend in radial and axial directions. Also, when the leg portions 86 are radially opposite to the inner surface 8, they are in resilient engagement therewith. The reversible stop means 80 is preferable formed from a metallic material, such as conventional piano wire, having a diameter of about 26-31 mils with the diameter of the opening 84 being about one mil greater to allow for free rotation of the central body portion 82. The distance between the leg portions 86 is greater than the diameter of the inner surface 8 but less than the diameter of the inner surface 14.

The hypodermic syringe 2 is assembled by cutting a radial slit (not shown) through the elongated rod 58 until it is in communication with the opening 84. Pressure is applied to the portions of the elongated rod 58 on opposite sides of the slit to open the slit so that the central body portion 82 can be moved through the slit into the opening 84. The end wall 16 is secured to the reversing chamber 6 by suitable means, such as by welding. The plug means 50 are then pushed onto the spear head 64 and the elongated rod 58 is then moved into and through the barrel portion 4, the reversing chamber 6 and the opening 18 in the end wall 16 while the plug means 50 moves into the first end portion 10. The needle means 30 are then placed against the plug means 50 and are pushed into the first end portion 10 and welded as described above. The handle 72 is then welded onto the first end portion 62. The assembled single use disposable hypodermic syringe 2 is illustrated in FIG. 3. The plug means 50 are in contact with or substantially in contact with the plastic body portion 32. The ends of the legs 86 are pointed toward the needle means 30 so that the plug means 50 can move in the direction of the arrow 88 but, when it has been moved away from the needle means 30, the plug means cannot be moved in the direction of the arrow 90.

In FIGS. 4 and 5, the single use disposable hypodermic syringe 2 is illustrated after it has been filled with the desired fluid 92. The abutment shoulder 74 has contacted the portions of the end wall 16 surrounding the opening 18 to prevent further movement of the plug means 50 in the direction of the arrow 88 so that the plug means 50 remain in the second end portion 12 and in sealing engagement with the inner surface 8. The reversible stop means 80 are located in the reversing chamber 6 so that the central body portion is free to rotate in the opening 84 and, as illustrated, has rotated so that the leg portions 86 are free to move. The axial length of leg portions 86, as illustrated in FIG. 3, is less than the axial distance between the radially inwardly extending wall 20 and the axis of rotation of the central body portion 82, as illustrated in FIG. 4, so that the leg portions 86 can move to the position illustrated in FIG. 4. As illustrated in FIG. 5, the distance between end portions 76 and 78 of the leg portions 86 is greater than the diameter of the inner surface 8 to ensure that the leg portions 86 are in resilient contact with the inner surface 8. In the position illustrated in FIG. 4, the single use hypodermic syringe 2 is now ready to inject the fluid 92 into a body (not shown).

In FIG. 6, the single use hypodermic syringe 2 is illustrated at a location partially through the operation of injecting the fluid 92 into a body. As the elongated rod 58 is moved from the illustration in FIG. 4 in the direction of the arrow 90, the leg portions 86 contact the juncture of the second end portion 12 and the radially inwardly extending wall 20, and the continued movement of the elongated rod 58 causes the central body portion 82 to rotate in the opening 84 until the ends of the leg portions 86 are pointing towards the reversing chamber 6. In this position, the elongated rod 58 can move the plug means 50 in the direction of the arrow 90 but the elongated rod 58 and the plug means 50 cannot be moved in the direction of the arrow 88. Thus, the movement of the elongated rod 58 and the plug means 50, if stopped before the plug means 50 reaches the plastic body portion 32, the elongated rod and the plug means 50 cannot be moved in the direction of the arrow 88 so that no more fluid 92 can be aspirated into the barrel portion 4. Also, when the plug means 50 move into contact with the plastic body portion 32, any attempt to move the elongated rod 58 in the direction of the arrow 88 will only dig the ends 76 and 78 of the leg portions 86 into the inner surface 8 to prevent movement of the elongated rod in the direction of the arrow 88.

The barrel portion 4 may have indicia provided thereon so that dosages of the fluid less than the capacity of the barrel portion may be administered. This can be accomplished in several ways. In one way, the hollow needle 34 can be inserted into a supply of the fluid and the elongated rod can be pulled to aspirate the desired amounts of fluid into the barrel portion 4. The hollow needle 34 is then withdrawn and the elongated rod is pulled until the reversible stop means 80 are in the reversing chamber 6. The hypodermic syringe 2 is then held in an upright position and the air will move to the top of the barrel portion 4. The elongated rod 58 is then pushed until all the air is removed from the barrel portion 4. In another way, the hollow needle 34 is inserted into a supply of the fluid and the elongated rod 58 is pulled to fill the barrel portion 4. The elongated rod 58 is then pushed to return all but the desired dosage of the fluid to the supply of the fluid.

In FIG. 7, there is illustrated a barrel portion 4 having opposite axially extending grooves 94 formed in the inner surface 8 and adapted to receive the end portions 76 and 78 of the leg portions 86.

It is contemplated that the inventive concepts herein described may be variously otherwise embodied and it is intended that the appended claims be construed to include the alternative embodiments of the invention except insofar as limited by the prior art.

What is claimed is:

1. A single use hypodermic syringe comprising:
   a hollow elongated barrel portion having a longitudinal axis, an inner surface and first and second end portions for use in providing a container for a fluid;
   needle means connected to said first end portion for permitting fluid to be drawn into or ejected from said barrel portion;
   plug means in sealing engagement with at least a portion of said inner surface and used to aspirate fluid into said barrel portion and to eject said fluid from said barrel portion;
   rod means having said plug means secured thereto and having a portion thereof projecting outwardly from said second end portion of said barrel portion for use in reciprocating said plug means along said longitudinal axis;
   reversible stop means for permitting movement of said plug means in one direction but preventing movement of said plug means in the opposite direction during the aspiration of fluid into said barrel portion and during or after the ejection of fluid from said barrel portion; and
   wherein said reversible stop means comprise:
   said rod means having an opening extending therethrough, having a longitudinal axis extending in a direction transverse to said longitudinal axis of said barrel portion;
   a rotatable stop member having a body portion located in said opening in said rod means for rotation about an axis transverse to the direction of movement of said plug means and at least one integral leg portion projecting radially and axially from said central body portion when said at least one integral leg portion is located within said barrel portion and said at least one integral leg portion being in resilient contact with said inner surface of said barrel portion; and
   reversing means integral with said barrel portion for reversing said reversible stop means after said fluid has been aspirated into said barrel portion.

2. The invention as in claim 1 wherein said reversing means comprise:
   a reversing chamber integral with said barrel portion; and
   said reversing chamber having a cross-sectional configuration larger than the cross-sectional configuration of said reversible stop member when said leg portion projects only in the radial direction.

3. The invention as in claim 2 and further comprising:
   an end wall secured to said reversing chamber and having an opening formed therein;
   said rod means passing through said opening; and
   said rod means substantially filling said opening.

4. The invention as in claim 3 and further comprising:
   stop means on said rod means for cooperating with the portions of said end wall surrounding said opening to limit the movement of said rod means.

5. The invention as in claim 3 and further comprising:
   rotation preventing means comprising a configuration of said rod means and said opening in said end wall for preventing rotation of said rod means.

6. The invention as in claim 1 wherein said reversible stop means comprise:
   a central body portion located in an opening in said rod means for rotation about an axis transverse to the direction of movement of said plug means;
   said opening having opposite open ends; and
   at least two leg portions, each of said leg portions projecting radially and axially from said central body portion through one of said openings and in resilient contact with said inner surface of said barrel portion.

7. A single use hypodermic syringe comprising:
   a hollow elongated barrel portion having a longitudinal axis, an inner surface and first and second end portions for use in providing a container for a fluid;
   needle means connected to said first end portion for permitting fluid to be drawn into or ejected from said barrel portion;

plug means in sealing engagement with at least a portion of said inner surface and used to aspirate fluid into said barrel portion and to eject said fluid from said barrel portion;

rod means having said plug means secured thereto and having a portion thereof projecting outwardly from said second end portion of said barrel portion for use in reciprocating said plug means along said longitudinal axis;

reversible stop means for permitting movement of said plug means in one direction but preventing movement of said plug means in the opposite direction during the aspiration of fluid into said barrel portion and during or after the ejection of fluid from said barrel portion; and wherein said reversible stop means comprise:
said rod means having an opening extending therethrough, said opening having a longitudinal axis extending in a direction transverse to said longitudinal axis of said barrel portion;
a rotatable stop member having a central body portion located in said opening for rotation therein;
at least two integral leg potions, each of said leg portions projecting radially and axially from said central body portion when located within said barrel portion and being in resilient contact with said inner surface of said barrel portion; and
reversing means integral with said barrel portion for reversing said reversible stop means after said fluid has been aspirated into said barrel portion.

8. The invention as in claim 7 wherein said reversing means comprises:
a reversing chamber integral with said barrel portion;
said reversing chamber having a cross-sectional configuration larger than the cross-sectional configuration of said inner surface of said barrel portion; and
force applying means for applying a force on said leg portions so that they extend in an axial direction toward said reversing chamber after leaving said reversing chamber during said ejection of fluid from said barrel portion.

9. The invention as in claim 8 and further comprising:
a pair of opposite longitudinally extending grooves in said inner surface of said barrel portion for receiving a portion of said legs.

10. The invention as in claim 7 wherein said needle means comprise:
a plastic body portion having a hollow needle projecting therefrom;
said plastic body portion having a generally cylindrical outer surface having a diameter slightly less than the diameter of said generally cylindrical inner surface of said barrel portion; and
sealing means for forming a fluid tight seal between said generally cylindrical inner and outer surfaces.

11. The invention as in claim 7 wherein:
said leg portions having end portions pointing toward said needle means during aspiration of said fluid into said barrel portion and pointing toward said reversing means during the ejection of fluid from said barrel portion.

12. The invention as in claim 7 wherein:
said opening in said rod having a cylindrical inner surface; and
said central body portion having a cylindrical outer surface having a diameter slightly less than the diameter of said inner surface to permit rotation of said central body portion in said opening.

13. The invention as in claim 7 wherein:
said rotatable stop member is formed from a metallic material.

14. The invention as in claim 7 wherein said reversing means comprises:
a reversing chamber integral with said barrel portion;
said reversing chamber having a cross-sectional configuration larger than the cross-sectional configuration of said reversible stop member when said leg portions project only in the radial direction; and
said cross-sectional configuration and the axial length of said reversing chamber being great enough to permit said leg portions to rotate after they move out of contact with said inner surface of said barrel portion, to a position where they project only in the radial direction.

15. The invention as in claim 14 and further comprising: an end wall secured on said reversing chamber and having an opening therein
rotation preventing means comprising a configuration of said rod means and said opening in said end wall for preventing rotation of said rod means.

16. The invention as in claim 15 and further comprising:
said rod means passing through said opening; and said rod means substantially filling said opening.

17. The invention as in claim 16 and further comprising:
stop means on said rod means for cooperating with the portions of said end wall surrounding said opening to limit the movement of said rod means.

18. The invention as in claim 16 wherein said rotation preventing means comprises:
said rod means having a non-circular cross-sectional configuration; and
said opening in said end wall having a cross-sectional configuration similar to that of said rod means to prevent rotation of said rod means.

19. The invention as in claim 18 wherein:
said barrel portion and said reversing chamber are formed from a plastic material; and
said rotatable stop member is formed from a metallic material.

20. The invention as in claim 19 wherein said needle means comprises:
a plastic body portion having a hollow needle projecting therefrom;
said plastic body portion having a generally cylindrical outer surface having a diameter slightly less than the diameter of said generally cylindrical inner surface of said barrel portion; and
sealing means for forming a fluid tight seal between said generally cylindrical inner and outer surfaces.

* * * * *